US010111585B2

(12) United States Patent
Inoue et al.

(10) Patent No.: US 10,111,585 B2
(45) Date of Patent: Oct. 30, 2018

(54) VISION TESTING DEVICE AND HEAD MOUNT TYPE DISPLAY DEVICE (71) Applicant: CREWT Medical Systems, Inc., Tokyo (JP)

(72) Inventors: Satoshi Inoue, Tokyo (JP); Kenzo Yamanaka, Tokyo (JP); Shinji Kimura, Tokyo (JP)

(73) Assignee: CREWT MEDICAL SYSTEMS, INC., Tokyo (JP)

( * ) Notice: Subject to any disclaimer, the term of this patent is extended or adjusted under 35 U.S.C. 154(b) by 0 days.

(21) Appl. No.: 15/520,546

(22) PCT Filed: Aug. 18, 2015

(86) PCT No.: PCT/JP2015/073070
§ 371 (c)(1),
(2) Date: Apr. 20, 2017

(87) PCT Pub. No.: WO2016/063600
PCT Pub. Date: Apr. 28, 2016

(65) Prior Publication Data
US 2017/0311794 A1 Nov. 2, 2017

(30) Foreign Application Priority Data
Oct. 20, 2014 (JP) ................ 2014-214015

(51) Int. Cl.
A61B 3/02 (2006.01)
A61B 3/032 (2006.01)
A61B 3/00 (2006.01)

(52) U.S. Cl.
CPC .............. A61B 3/032 (2013.01); A61B 3/005 (2013.01); A61B 3/0083 (2013.01)

(58) Field of Classification Search
CPC ....... A61B 3/032; A61B 3/0091; A61B 3/024; A61B 3/028; A61B 3/0033
(Continued)

(56) References Cited

U.S. PATENT DOCUMENTS 5,909,317 A * 6/1999 Nakaoka ............ G02B 27/0025
359/631
6,008,778 A * 12/1999 Takahashi .......... G02B 27/0172
345/7
(Continued)

FOREIGN PATENT DOCUMENTS

JP H07-151993 A 6/1995
JP H09-133890 A 5/1997
(Continued)

OTHER PUBLICATIONS

Nov. 17, 2015 International Search Report issued with International Patent Application No. PCT/JP2015/073070.
(Continued)

Primary Examiner — Mohammed Hasan
(74) Attorney, Agent, or Firm — Oliff PLC (57) ABSTRACT When displaying visual targets on a planar display element and performing vision examinations, the size of the visual target visible to the subject changes according to the position at which the visual target is displayed. This vision examination device includes: a planar display element that displays visual targets to a subject of a vision examination; and a display optical system provided upon an optical axis between an eyeball position at which an eyeball of the subject is arranged and a display screen of the planar display element. The display optical system includes an f-θ optical system having a proportional relationship between an image height on the display screen of the planar display element and the angle of incidence θ for the main light rays when the (Continued)

subject views the visual target through the display optical system from the eyeball position.

4 Claims, 4 Drawing Sheets

(58) Field of Classification Search
USPC .................................................. 351/200–246
See application file for complete search history.

(56) References Cited

U.S. PATENT DOCUMENTS

2009/0219484 A1    9/2009   Ebisawa
2014/0118685 A1    5/2014   Kawamura

FOREIGN PATENT DOCUMENTS

| | | |
|---|---|---|
| JP | H11-23984 A | 1/1999 |
| JP | 2004-020590 A | 1/2004 |
| JP | 2006-280665 A | 10/2006 |
| JP | 4518077 B2 | 8/2010 |
| JP | 2010-237638 A | 10/2010 |
| JP | 2012-020196 A | 2/2012 |
| JP | 2014-100254 A | 6/2014 |

OTHER PUBLICATIONS

Jun. 27, 2018 Extended Search Report issued in European Patent Application No. 15853596.3.

\* cited by examiner

VISION TESTING DEVICE AND HEAD MOUNT TYPE DISPLAY DEVICE

TECHNICAL FIELD

The present invention relates to a vision testing device and a head mount type display device.

DESCRIPTION OF RELATED ART

A "vision test" for testing a visual function of an eye, is mentioned as one of eye tests. Further, "visual field test" is mentioned as a typical vision test. The visual field test is performed for diagnosis of visual field narrowing, visual field defect, and the like caused by, for example glaucoma, retinal detachment and the like, and various testing devices have been proposed for this purpose.

A conventional visual field testing device includes a device that displays (presents) a visual target on a dome type screen and tests a visual field of a testee (see, for example, Patent Document 1). In this type of the visual field testing device, an eyeball of the testee (hereinafter also referred to as "a tested eye") is placed on the spherical center of a dome, and when the testee looks at the screen from there, for example to what extent the visual target can be viewed or which position of the visual target cannot be viewed, is tested.

On the other hand, patent document 2 describes a visual field testing device (perimeter) that displays a visual target for a testee using a planar display device. In this visual field testing device, the planar display device is installed in a large case so as not to be affected by external light or the like. Then, a head of the testee is fixed by supporting the testee's jaw from below, so that the testee can see a display surface of the planar display device through a peephole on the side surface of the case in this state.

PRIOR ART DOCUMENT

Patent Document

Patent document 1: Japanese Patent Laid Open Publication No. 2012-20196
Patent document 2: Patent Publication No. 4518077

SUMMARY OF THE INVENTION

Problem to be Solved by the Invention

When a visual field test is performed by displaying a visual target on a dome type screen, the way the visual target is viewed from the testee basically does not change regardless of a position on the screen where the visual target is displayed, if the visual target has the same size. On the other hand, when the visual field is tested by displaying the visual target on the display surface of the planar display device, the way the visual target is viewed from the testee changes even in a case of the visual target having the same size, depending on the position of the visual target displayed on the display surface.

Specifically, even in a case of the visual target having the same size, when it is displayed at a center portion of the display surface and when it is displayed at a peripheral portion thereof, the size of the visual target viewed from the testee becomes smaller in the latter case. The reason is as follows. First, when the visual target is displayed on the display surface of the planar display device and the testee views the visual target through a lens, a relationship between an incident angle $\theta$ and an image height Y is $Y = f \cdot \tan \theta$ (where f is a focal length). This relational expression means that the image height Y is increased in accordance with a $\tan \theta$ curve, when an incident angle $\theta$ is increased at a constant rate.

The above relationship becomes as follows, when considering a case that it is replaced with a visual field test. In other words, when the display surface of the planar display device is configured by a large number of pixels disposed in a matrix and the visual target is displayed with the size of a specified number of pixels on the display surface, the size of the visual target viewed from the testee is changed depending on a display position of the visual target even if the size of the visual target displayed on the display surface is the same. Specifically, the visual target displayed at the center of the display surface appears larger than the visual target displayed at the peripheral portion thereof. Particularly in a case of the visual field test, it is necessary to secure a sufficiently wide viewing angle in order to diagnose whether or not a field of vision of the testee is provided at a normal level. For this reason, the way the visual target is viewed, is more influenced by an increase in the image height based on the $\tan \theta$ curve.

The size of the visual target viewed from the testee means the size of an image of the visual target formed on a retina of the testee when the testee views the visual target through a lens.

A principal object of the present invention is to provide a vision testing device capable of forming an image of a visual target with the same size on the retina of the testee regardless of the display position of the visual target, if the size of the visual target displayed on the display surface of the planar display device is the same, when the vision test is performed by displaying the visual target on the planar display device.

Means for Solving the Problem

According to an aspect of the present invention, there is provided a vision testing device, including:
a planar display device that displays a visual target for a testee who receives a vision test; and
a display optical system provided on an optical axis between an eyeball position where an eyeball of the testee is placed and a display surface of the planar display device,
wherein the display optical system is configured by a f-$\theta$ optical system in which a relationship between an incident angle of a principal ray when the testee views a visual target from the eyeball position through the display optical system and an image height on a display surface of the planar display device is proportional.

According to a second aspect of the present invention, there is provided the vision testing device of the first aspect, wherein the display optical system includes a plurality of lenses disposed in an order from the eyeball position and at least a lens closest to the eyeball position among the plurality of lenses is configured as an aspheric lens.

According to a third aspect of the present invention, there is provided the vision testing device of the first or second aspect, wherein a maximum viewing angle of the display optical system is set in a range of 30 degrees or more and 60 degrees or less at a half angle of view.

According to a fourth aspect of the present invention, there is provided a head mount type display device used by being mounted on a user's head, including:
a planar display device that displays an image for a user; and a display optical system provided on an optical axis between an eyeball position where an eyeball of the user is placed and the display surface of the planar display device, wherein the display optical system is configured by a f-θ optical system in which a relationship between an incident angle of a principal ray when the testee views an image from the eyeball position through the display optical system and an image height on a display surface of the planar display device is proportional.

Advantage of the Invention

According to the present invention, an image of a visual target can be formed with the same size on the retina of the testee regardless of the display position of the visual target, if the size of the visual target displayed on the display surface of the planar display device is the same, when the vision test is performed by displaying the visual target on the planar display device.

DETAILED DESCRIPTION OF THE INVENTION

Embodiments of the present invention will be described hereafter, with reference to the drawings.

In this embodiment, explanation is given for a case in which the present invention is applied to a head mount type vision testing device.

Further, the embodiment of the present invention will be described in the following order.
1. Configuration of a vision testing device
2. Characteristic of a display optical system
3. Vision testing method
4. Effect of the embodiment
5. Another embodiment
6. Modified example, etc.

<1. Configuration of a Vision Testing Device>

Figure 1:
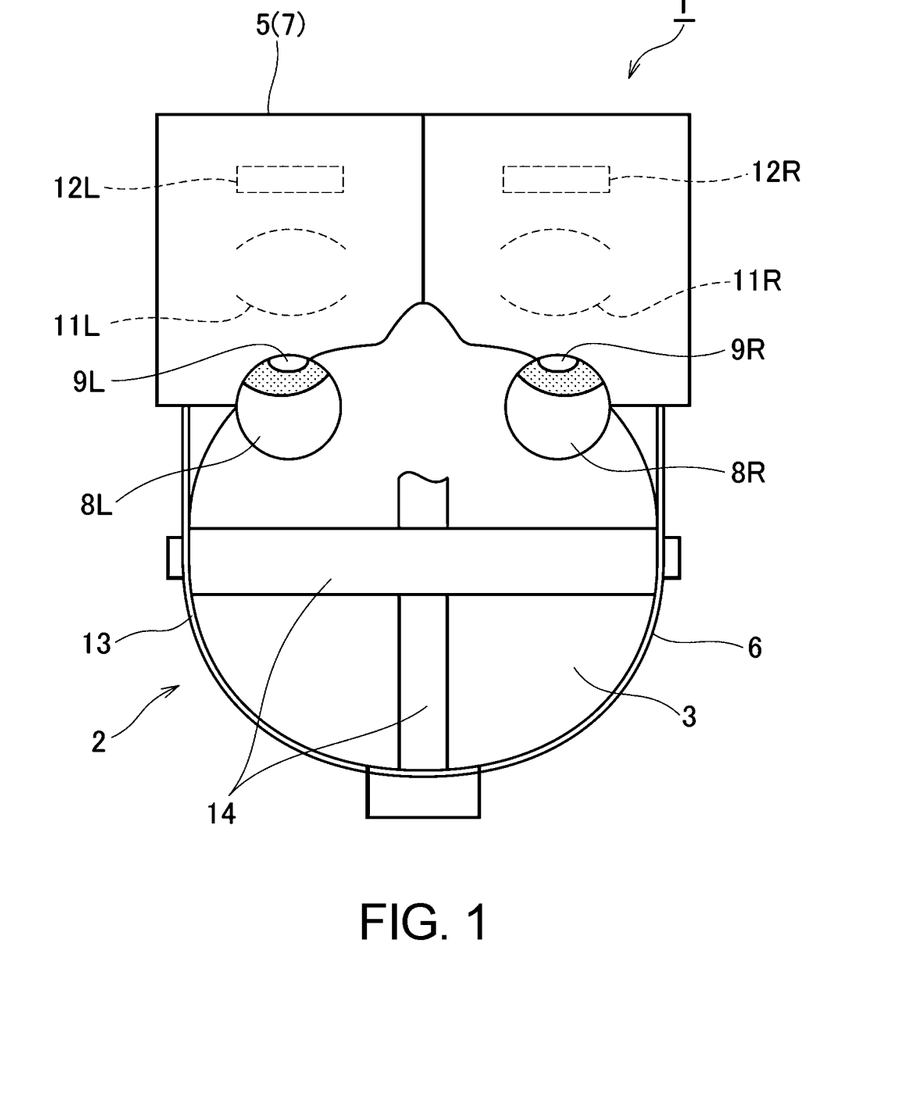
FIG. 1 is a schematic view showing a configuration example of a vision testing device according to an embodiment of the present invention.

FIG. 1 is a schematic view showing a configuration example of a vision testing device according to an embodiment of the present invention.

A vision testing device 1 shown in the figure is a head mount type vision testing device used by being mounted on a head 3 of a testee 2. The vision testing device 1 roughly includes an device main body 5 and an mounting fixture 6 mechanically connected to the device main body 5.

The device main body 5 includes a casing 7 having a space inside. An internal space of the casing 7 is divided into left and right. The reason thereof is to perform vision test separately for a left eye 8L and a right eye 8R of the testee 2. When the left eye 8L is used as the eye to be tested in this vision test, the testee 2 views the visual target through a pupil 9L of the left eye 8L, and when the right eye 8R is used as the eye to be tested in this vision test, the testee 2 views the visual target through a pupil 9R of the right eye 8R.

The term "visual target" described here is displayed for giving a stimulus by light to the eyeball of the testee when testing the vision of the testee. Regarding the visual target, there is no particular limitation on size and shape, etc. For example, at the time of a glaucoma test, presence or absence of a missing field of view and a location of a defect can be tested (specified) by displaying a point of light as a visual target with a predetermined size, and changing a position of the point of the light.

A display optical system 11L and a planar display device 12L are provided in one internal space of the casing 7. A display optical system 11R and a planar display device 12R are provided in the other internal space of the casing 7. The display optical system 11L and the planar display device 12L are provided for visually testing the left eye 8L of the testee 2. The display optical system 11R and the planar display device 12R are provided for visually testing the right eye 8R of the testee 2.

A mounting fixture 6 is provided for mounting and fixing the device main body 5 to the head 3 of the testee 2. The mounting fixture 6 includes a belt 13 wound in a U-shape from both sides of a head to a rear head side of the testee 2, and a belt 14 wound around a head top of the testee 2. Then, the mounting fixture 5 has a mechanism such that by pulling and tightening the belt 13 from the rear head side in a state that a length of the belt 14 is adjusted appropriately, the device main body 5 can be mounted on the head 3 of the testee 2.

In the description hereafter, when the left eye 8L and the right eye 8R of the testee 2 are described without distinction between left and right, letters L and R are omitted so that the left eye 8L and the right eye 8R are collectively called an eyeball 8 and a pupil 9. Similarly, when the abovementioned display optical systems 11L, 11R and planar display devices 12L, 12R are described without distinction between left and right, letters L and R are omitted so that the display optical systems 11L and 11R are collectively called a display optical system 11, and the planar display devices 12L and 12R are collectively called a planar display device 12.

Figure 2:
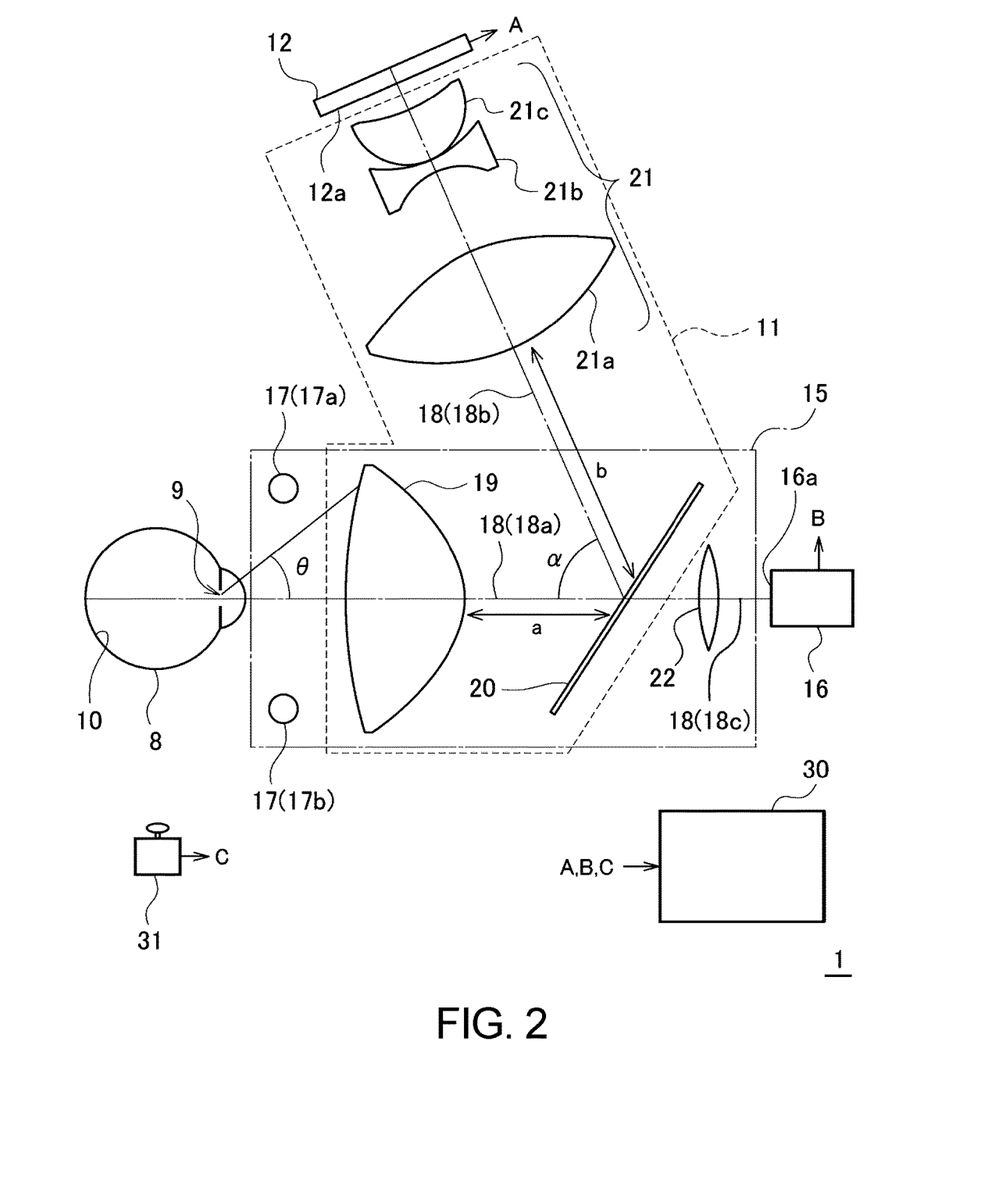
FIG. 2 is a view showing an example of an optical configuration of the vision testing device according to an embodiment of the present invention.

FIG. 2 is a view showing an example of an optical configuration of the vision testing device according to an embodiment of the present invention.

As shown in the figure, the vision testing device 1 includes an observation optical system 15 for observing the eyeball 8 of the testee; an imaging device 16 for imaging the eyeball 8 of the testee through the observation optical system 15; an infrared light source 17 that irradiates the eyeball 8 of the testee with infrared rays; a controller 30, and a response switch 31, in addition to the abovementioned display optical system 11 and planar display device 12. Similarly to the abovementioned display optical system 11 and planar display device 12, the observation optical system 15, the imaging device 16, and the infrared light source 17 are provided separately for the left eye and the right eye of the testee, and the controller 30 and the response switch 31 are provided for each vision testing device 1, one by one.

The display optical system 11 is provided on the optical axis 18 between the eyeball position where the eyeball 8 of the testee is placed and the display surface 12a of the planar display device 12. Specifically, the display optical system 11 has a configuration in which a first lens 19, a mirror 20, and a second lens group 21 are disposed in an order from the eyeball position side of the testee. Each configuration element will be descried hereafter. In the following description, an optical axis from a position of an eyeball to a mirror 20 is set as an optical axis 18a, and an optical axis from the mirror 20 to the planar display device 12 is set as an optical axis 18b, out of the optical axis 18 from the eyeball position of the testee to the planar display device 12.

The first lens 19 is disposed on the optical axis 18a from the eyeball position to the mirror 20. The first lens 19 is configured using an aspherical lens (convex lens) having a positive power. The first lens 19 converges a light reflected by the mirror 20 and incident on the first lens 19 to the pupil 9 of the testee while suppressing a divergence of the light when the testee views an object through the pupil 9 at a wide angle. In FIG. 2, a point of light serving as a visual target is displayed on the display surface 12a of the planar display device 12, and an angle of incidence of the principal ray incident on the first lens 19 from the center of the pupil of the testee when the testee views this visual target from the eyeball position through the display optical system 11, is indicated by a symbol θ. The incident angle θ is an angle with respect to the optical axis 18a (the angle formed by the principal ray passing through the pupil center and the optical axis 18a). The outer diameter (diameter) and the position of the first lens 19 on the optical axis 18a are set under conditions that can secure a viewing angle necessary for at least a vision test. Specifically, a maximum viewing angle (a maximum value of θ) of the display optical system 11 using the first lens 19 is preferably not less than 30 degrees and not more than 60 degrees (60 degrees or more and 120 degrees or less in all viewing angle).

The mirror 20 is disposed on the side opposite to the eyeball position interposing the first lens 19 therebetween, on the optical axis 18a from the eyeball position to the mirror 20. The mirror 20 is configured using a mirror having wavelength selectivity. Specifically, the mirror 20 is configured using a cold mirror that reflects a visible light and transmits an infrared ray. An inclination of a reflection surface of the mirror 20 with respect to the optical axis 18a is set such that an angle α formed between the optical axis 18a and the optical axis 18b bent by the mirror 20, is preferably 90 degrees or less, more preferably 80 degrees or less, and further preferably in a range of "40 degrees<α<70 degrees".

Here, in a case of α≤40°, there is a possibility that the planar display device 12 and the second lens group 21 are too close to the head of the testee, and they interfere with the head. On the other hand, in a case of α>40°, it is possible to avoid the planar display device 12 and the second lens group 21 from interfering with the head. On the other hand, in a case of α≥90°, when the testee tilts the head forward, the vision testing device 1 is likely to fall off from the head. On the other hand, in a case of α<90°, when the testee tilts the head forward, the vision testing device 1 is less likely to fall off from the head.

The second lens group 21 is disposed on the optical axis 18b from the mirror 20 to the planar display device 12. The second lens group 21 is configured using three lenses 21a, 21b, and 21c. The three lenses 21a, 21b, and 21c are sequentially disposed from the mirror 20 side toward the planar display device 12 side. In other words, the lens 21a is disposed at a position closest to the mirror 20 on the optical axis 18b, and the lens 21c is disposed at the position closest to the planar display device 12 on the optical axis 18b. Then, a lens 21b is disposed between the two lenses 21a and 21c. The lens 21b is disposed close to the lens 21c in a state of being separated from the lens 21a.

The lens 21a is configured using an aspherical lens (convex lens) having a positive power. Also, the lens 21b is configured using an aspherical lens (concave lens) having a negative power, and the lens 21c is configured using an aspheric lens (convex meniscus lens) having a positive power. An outer diameter (diameter) of the lens 21a is larger than outer diameters of the other lenses 21b, 21c, and the outer diameters of the lenses 21b, 21c are substantially equal to each other.

Here, when the Abbe number of a material constituting the first lens 19 is v1, the first lens 19 is made of a material (glass, plastic, etc.) that satisfies the relational expression "45<v1<80". On the other hand, when the Abbe numbers of the lenses 21a and 21c having a positive power among the lenses 21a to 21c constituting the second lens group 21 are both v2, each lens 21a and 21c is made of a material satisfying the relational expression "45<v2<80". Also, when the Abbe number of the lens 21b having a negative power is v3, the lens 21b is made of a material satisfying the relational expression "15<v3<30". Further, when a focal length of the first lens 19 is f1 and a focal length of the second lens group 21 is f2, they satisfy the relational expression "0<f1/f2<1.0". Further, the focal length f1 of the first lens 19 is shorter than the sum (a+b) of the optical distance a from the first lens 19 to the mirror 20 and the optical distance b from the mirror 20 to the second lens group 21 (lens 21a).

The planar display device 12 is disposed so as to face the lens 21c of the second lens group 21 on the optical axis 18b from the mirror 20 to the planar display device 12. The planar display device 12 is configured using, for example a liquid crystal display device having a backlight. The display surface 12a of the planar display device 12 has a configuration in which a large number of pixels are disposed in a matrix. When an image (including a visual target) is actually displayed on the display surface 12a, display and non-display (on/off) of the image can be controlled on a pixel basis. The display surface 12a of the planar display device 12 preferably has a display size in which a diagonal length is 1.5 inches or less, more preferably a display size in which a diagonal length is 1 inch or less, and the optical axis 18b is aligned with a center of the display surface 12a.

In the display optical system 11 and the planar display device 12 having the above configuration, when the visual target is displayed on the display surface 12a of the planar display device 12, the testee 2 views the visual target from the eyeball position through the first lens 19, the mirror 20, and the second lens group 21. In such a case, by enlarging an outer diameter of the first lens 19 closest to the eyeball position, the vision test can be performed in a wider range. However, when the outer diameter of the first lens 19 is increased, the principal ray passing through a lens edge is greatly inclined with respect to the optical axis 18 (18a). Therefore, when the power of the first lens 19 is low, the principal ray passing through the lens edge is diverged.

Therefore, in this embodiment, by using a lens having a high power (preferably a power of 20 D (dioptre) or more and 60 D or less) for the first lens 19, the principal ray passing through the lens edge of the first lens 19 is largely refracted to be settled on a reflection surface of the mirror 20. However, when such a high power first lens 19 is used, a light flux of the principal ray is converged and focused in the middle of an optical path from the first lens 19 to the second lens group 21. Therefore, the second lens group 21 is disposed on the optical axis 18b in order to converge (form) the image of the light flux of the principal ray again which is focused in the middle of the optical path on the display surface 12a of the planar display device 12. Further, in order to correct chromatic aberration and image magnification, the second lens group 21 is composed of three lenses 21a, 21b and 21c.

The observation optical system 15 is provided for observing, for example an anterior eye part including the pupil 9, an iris, a sclera and the like, or an eye fundus including the retina 10, using the eyeball 8 of the testee as an observation target. The observation optical system 15 is provided on the optical axis 18 from the eyeball position of the testee to the imaging device 16. Specifically, the observation optical system 15 has a configuration in which the first lens 19, the mirror 20, and the third lens 22 are disposed in an order from the eyeball position side of the testee. Among them, the first lens 19 and the mirror 20, including the optical axis 18a, are common (shared) with the abovementioned display optical system 11. Further, when the optical axis from the mirror 20 to the imaging device 16 is the optical axis 18c, the optical axis 18c is substantially parallel to the abovementioned optical axis 18a.

The third lens 22 is disposed on the optical axis 18c from the mirror 20 to the imaging device 16. The third lens 22 is configured using an aspheric lens (convex lens) having a positive power. When the eyeball 8 is observed using the first lens 19 as an objective lens, the third lens 22 functions so that an image of a light incident on the first lens 19 from the eyeball 8 and passing through the mirror 20, is formed on the imaging surface 16a of the imaging device 16.

The imaging device 16 picks up (images) an image of the eyeball (an anterior eye part, an eye fundus, etc.) 8 to be tested. The imaging device 16 is configured using a CCD (Charge Coupled Device) imaging device, a CMOS (Complementary Metal Oxide Semiconductor) imaging device, and the like, having sensitivity to infrared rays. The imaging surface 16a of the imaging device 16 is disposed on the optical axis 18c in a direction facing the eyeball 8, and the optical axis 18c is aligned with the center of the imaging surface 16a.

The infrared light source 17 performs irradiation of an infrared ray toward the eyeball position of the testee. The infrared light source 17 is configured using a pair of infrared light emitting diodes 17a and 17b. The pair of infrared light emitting diodes 17a and 17b are disposed obliquely upward and obliquely downward with respect to the eyeball position of the testee so as not to obstruct the field of view of the testee. Then, one of the infrared light emitting diodes 17a emits the infrared ray from obliquely upward of the eyeball 8 of the testee and the other infrared light emitting diode 17b emits the infrared ray from obliquely downward of the eyeball 8 of the testee.

In the observation optical system 15 and the imaging device 16 having the above configuration, the image of the eyeball 8 is imaged by the imaging device 16 through the first lens 19, the mirror 20, and the third lens 22 while emitting the infrared light from the infrared light source 17 to the eyeball 8 of the testee.

The controller 30 realizes various functions (means) when the vision test is performed. For example, the controller 30 has a smaller casing structure than the device main body 5, and is disposed so as to be mounted on the rear head side of the mounting fixture 6. Thereby, it is possible to maintain a weight balance in the front and rear of the device main body 5 and the controller 30.

The controller 30 is configured by a computer including a combination of a CPU (Central Processing Unit), RAM (Random Access Memory), ROM (Read Only Memory), HDD (Hard Disk Drive), various interfaces, and the like.

Then, the controller 30 is configured to realize various functions by the CPU executing a predetermined program stored in the ROM or the HDD. As an example of the functions (means) realized by execution of the program, the controller 30 has a function of controlling an operation of each unit such as the display device 12, the imaging device 16, and the infrared light source 17, etc. incorporated in the device main body 5. A predetermined program for realizing each function is installed in a computer and used, or may be provided by being stored in a computer readable storage medium before installation, or may be provided through a communication line connected to the computer.

The response switch 31 is provided for performing a switching operation by the testee. When the testee depresses the response switch 31, ON signal is outputted from the response switch 31 at that moment. This ON signal is incorporated into the controller 30. The response switch 31 is provided as a manual type operated by the testee by holding it in his/her hand. However, the response switch 31 is not limited thereto, and a foot-operated switch may also be used.

<2. Characteristic of the Display Optical System>

The display optical system 11 according to this embodiment is an optical system having f-θ characteristic. The "f-θ characteristic" described here means an optical characteristic in which the relationship between the incident angle θ of the principal ray when the testee views the visual target from the eyeball position through the display optical system 11, and the image height Y on the display surface 12a of the planar display device 12 has a proportional relationship.

In this embodiment, the first lens 19 and each of the lenses 21a, 21b, 21c of the second lens group 21 is prepared as an aspheric lens having a predetermined refractive index, and by combining these plural lenses, the f-θ characteristic is realized in the entire display optical system 11. However, in order for the display optical system 11 to have the f-θ characteristic, it is not necessary to make all the lenses constituting the display optical system 11 as aspheric lenses, and for example, the f-θ characteristic can be realized by a combination of a plurality of spherical lenses or a combination of a spherical lens and an aspherical lens. In such a case, among the plurality of lenses constituting the display optical system 11, a lens closest to the eyeball position (the first lens 19 in this embodiment) is preferably constituted as the aspherical lens. This is because when the lens closest to the eyeball position is constituted as an aspherical lens, reduction in the number of lenses is expected because freedom of optical design is increased compared to a case of using the lens as a spherical lens, and the size and weight of the vision testing device 1 can be reduced. In particular, forming a long optical path from the eyeball position to the mirror 20, means that the device main body 5 becomes long in front of the testee, thus causing a problem that it is difficult to ensure a weight balance. Therefore, it is preferable that the lens closest to the eyeball position is set as an aspherical lens and an amount of protrusion in front of the testee is reduced as small as possible.

<3. Vision Testing Method>

By using the visual testing device 1 having the above configuration, it is possible to perform dynamic quantitative visual field examination (Goldman visual field examination), static quantitative visual field examination, fundus visual field examination (microperimetry), electroretinogram (ERG) and other examination. Here, as an example, a case of performing the static quantitative visual field examination will be described.

The static quantitative visual field examination is performed as follows. First, the visual target is presented at one point in the field of view, and its brightness is gradually increased. When the brightness of the visual target reaches a certain level, the visual target becomes visible from the testee. Then, a value corresponding to the brightness sufficient for the testee to view the visual target, is defined as a retina sensitivity at a point where the visual target is presented at that time. Then, by performing a similar measurement for each point in the field of view, difference in the retina sensitivity within the field of view is quantitatively examined, to thereby create a map. Such a static quantitative visual field examination has a subjective examination and an objective examination. By using the vision testing device 1 of this embodiment, any type of examination can be performed. Explanation will be given hereafter.

The subjective examination is performed as follows. First, a head mount type vision testing device 1 is mounted on the testee's head. Further, the testee is made to have the response switch 31 in the hand. Next, based on a command from the controller 30, a visual target for visual field test is displayed at one point on the display surface 12a of the planar display device 12. At this time, the brightness of the visual target is made dark at first, and thereafter, the brightness of the visual target is gradually increased. Then, even if the brightness of the visual target is dark at first and the visual target cannot be viewed from the testee, the retina of the testee responds to a light stimulus when the brightness of the visual target reaches a certain level, and the visual target becomes visible from the testee. Therefore, when the visual target becomes visible from the testee, the testee is asked to press the response switch 31. When the testee presses the response switch 31, ON signal is sent to the controller 30. Upon receiving this ON signal, the controller 30 performs a predetermined processing, and the value corresponding to the brightness of the point of the visual target at that time is set as the sensitivity of the retina at that point. Thereafter, by performing the same measurement for each point in the visual field, difference in the retina sensitivity within the field of view is quantitatively examined, to thereby create a retina sensitivity map.

The objective examination is performed as follows. First, the head mount type vision testing device 1 is mounted on the testee's head. In this case, it is not necessary for the testee to have the response switch 31 in the hand. Next, the visual target for the vision test is displayed at one point on the display surface 12a of the planar display device 12, based on a command from the controller 30. At this time, at first, the brightness of the visual target is made dark, and thereafter, the brightness of the visual target is gradually increased. Then, even if the brightness of the visual target is dark at first and the visual target cannot be viewed from the testee, the retina of the testee responds to a light stimulus when the brightness of the visual target reaches a certain level, and the visual target becomes visible from the testee.

At that time, the size (pupil diameter) of the pupil 9 of the testee changes according to the brightness of the visual target. Specifically, the diameter of the pupil 9 of the testee is reduced. A state change of the eyeball 8 at this time is imaged. Imaging of the eyeball 8 is performed in such a way that the eyeball 8 is irradiated with an infrared ray from the infrared light source 17, and an image of the light of the eyeball 8 obtained thereby is formed on the imaging surface 16a of the imaging device 16 via the observation optical system 15 (19, 20, 22). The timing for starting the imaging of the eyeball 8 may be set, for example at the timing before displaying the visual target on the display surface 12a, or at the same time as displaying the visual target. Since the human retina is not sensitive to infrared rays, the infrared rays don't affect the state change of the eyeball 8.

Image data of the eyeball 8 imaged by the imaging device 16 is incorporated into the controller 30. In the process of gradually increasing the brightness of the target, the controller 30 judges whether a pupil diameter of the testee has changed (reduced) in response to the brightness of the visual target, based on the image data sent from the imaging device 16. Then, when it is judged that the pupil diameter of the testee is changed, the value corresponding to the brightness of the point of the visual target at that time is set as the sensitivity on the retina at that point. Thereafter, similar measurements are automatically performed one after another for each point in the field of view, and the difference in the sensitivity on the retina is quantitatively examined, to thereby automatically create the sensitivity map.

Further, in the objective examination, a single suprathreshold stimulus method may be used, in which a bright visual target is displayed at one point on the display surface 12a of the planar display device 12, and the degree of reduction in pupil diameter is observed, to thereby create the sensitivity map.

<4. Effect of the Embodiment>

In performing the vision test including the abovementioned visual field test, the following effect can be obtained according to the vision testing device 1 of this embodiment.

First, prior to description of the effect, the optical characteristic of the display optical system 11 will be described with reference to FIG. 3.

Figure 3:
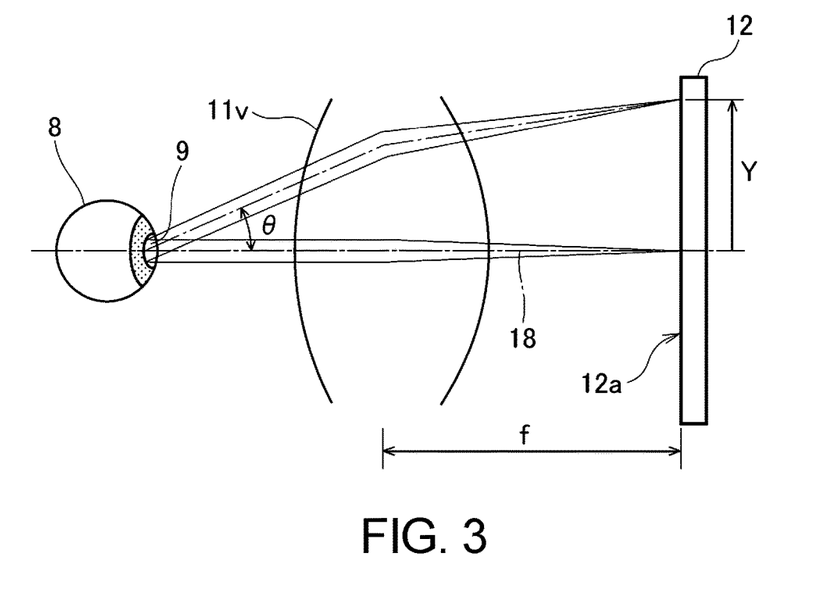
FIG. 3 is a view for describing characteristics of a display optical system.

In FIG. 3, the following case is assumed: the pupil 9 of the eyeball 8 is used as an exit pupil, the principal ray passes through the center (pupil center) of this exit pupil, and the light flux of the principal ray is focused on the display surface 12a of the planar display device 12 to form an image thereon, and the display surface 12a is used as a surface on which an image of the light flux of each principal ray is formed. In this state, the testee 2 views the display surface 12a. In addition, the first lens 19, the mirror 20, and the second lens group 21 constituting the display optical system 11 are replaced with one virtual lens (f-θ lens) 11v and displayed. Then, the focal length of the lens 11v is represented by f, the incident angle of the principal ray with respect to the lens 11v is represented by θ, and the image height on the display surface 12a is represented by Y. In this case, the focal length f of the lens 11v corresponds to the focal length of the entire lenses including the first lens 19 and the second lens group 21.

Figure 4:
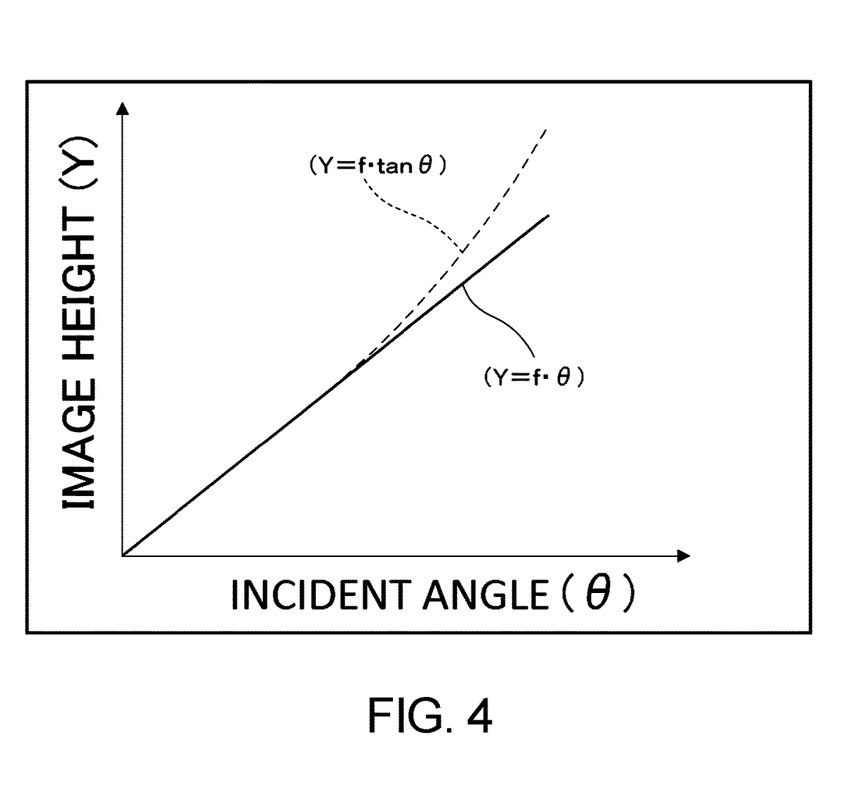
FIG. 4 is a view showing a relationship between an incident angle θ and an image height Y.

FIG. 4 is a graph showing a relationship between the image height Y indicated by the vertical axis, and the incident angle θ indicated by the horizontal axis. The solid line in the figure shows a case where the relationship between the incident angle θ and the image height Y is proportional (Y=f·θ), and the dotted line in the figure shows a case where Y=f·tan θ.

In this embodiment, the display optical system 11 is configured by the f-θ optical system, and therefore the relationship between the incident angle θ and the image height Y is a proportional relationship. Accordingly, for example, when it is assumed that the incident angle θ to the lens 11v has changed from 0 degrees to 60 degrees, the image height Y on the display surface 12a of the planar display device 12 is changed at the same rate (magnification) as the incident angle θ, accompanying the change of the incident angle θ.

Thus, when the size of the visual target displayed on the display surface 12a of the planar display device 12 is defined by the number of pixels, the visual effect per pixel given to the testee is the same, whichever the position of the visual target is on the optical axis or outside of the optical axis. In other words, even if the incident angle θ is changed, when the size of the target displayed on the display surface 12a is the same, it is possible to form the image of a target with the same size on the retina 10 of the testee, regardless of the display position of the visual target. Accordingly, when the visual target is displayed having the size of the specified number of pixels on the display surface 12a of the planar display device 12, the size of the visual target viewed from the testee is the same regardless of the display position of the visual target, when the size of the visual target displayed on the display surface 12a is the same. As a result, even when the planar display device 12 is used for displaying the target, it becomes possible for the testee to visually recognize the visual target having the size as prescribed, throughout the inspection range of the vision test.

When an optical system satisfying the relationship Y=f·tan θ is adopted as the display optical system 11, the proportional relationship between the incident angle θ and the image height Y disappears (see the dotted line in FIG. 4) when the incident angle θ becomes larger than a certain value. Then, as the incident angle θ is increased, the amount of increase in the image height Y is increased. Accordingly, even if the visual target of the same size is displayed on the display surface 12a of the planar display device 12, the visual effect per pixel given to the testee is changed depending on whether the display position is on the optical axis or out of the optical axis. This tendency becomes more prominent as the incident angle θ is increased.

Further, when the optical system having the above characteristic is applied to the head mount type vision testing device 1, a pincushion type deformation is perceived on the peripheral portion of the display surface 12a, when the entire display surface 12a of the planar display device 12 is made observable for the testee.

However, the present embodiment adopts a configuration in which the field of view when the testee views the display surface 12a from the eyeball position is narrowed down by the lenses (19, 21) of the display optical system 11. Therefore, if the outer shape of each lens (19, 21) is circular as viewed from an optical axis direction, the field of view is circular due to the effect of narrowing down of the field of view by this lens frame. In that case, no deformation of the pincushion type is perceived at the peripheral portion of the display surface 12a.

<5. Other Embodiment>

The present invention can be embodied not only as a vision testing device but also as a head mount type display device (Head Mounted Display). In this case, "testee" is replaced with "user" as a configuration of the head mount type display device, and constituent elements (the imaging device 16, the infrared light source 17, the third lens 22) specialized for the vision test are not required among the constituent elements of the abovementioned vision testing device 1. In other words, the eyeball 8 of the user using the head mount type display device is disposed at the eyeball position, the first lens 19, the mirror 20, the second lens group 21, and the planar display device 12 are disposed on the optical axis 18 (18a, 18b) in this order from the eyeball position side.

Regarding the configuration of the display optical system 11, the mirror 20 is not indispensable and it may be provided as necessary. When the mirror 20 is not provided, the optical axis from the position of the eyeball to the display surface 12a of the planar display device 12 is made straight and the first lens 19 and the second lens group 21 are disposed on this optical axis. The image displayed on the display surface 12a of the planar display device 12 is not particularly limited and may be any of still images, moving images (games, movie images, etc.). Also, the image to be displayed is not limited to a two-dimensional image but may be a three-dimensional image with parallax on the left and right.

When the display optical system 11 of the head mount type display device is an f-θ optical system, there is a concern that the peripheral portion of the image (image) displayed on the display surface 12a of the planar display device 12 may be slightly distorted due to the distortion characteristic by the f-θ optical system. However, as long as it is an optical system which has the effect equivalent to the abovementioned effect of narrowing the field of view and in which entire display surface 12a of the planar display device 12 cannot be visually recognized, distortion in the peripheral part is not perceived. Particularly in the case of the head mount type display device or the like which allows a user to experience virtual reality, the viewing angle is kept very large to show the image to the user, in many cases. In such a case, the visual effect due to the f-θ characteristic provides a great merit of displaying a more detailed image. In particular, it is preferable to set a maximum viewing angle θ-max of the display optical system 11 in a range of 30 degrees or more and 60 degrees or less.

<6. Modified Example>

The technical scope of the present invention is not limited to the abovementioned embodiment, and includes various modifications and improvements in a range capable of deriving a specific effect obtained by the constituting features of the invention and a combination of them.

For example, in the abovementioned embodiment, the mounting fixture 6 of the vision testing device 1 is configured by using the belts 13 and 14. However, any type of the mounting fixture 6 may be adopted as long as the device main body 5 can be mounted on the head 3 of the testee 2. However, if the position of the device body 5 moves during the vision test, a correct test result cannot be obtained. Therefore, as a configuration of the mounting fixture 6, it is preferable that the main body 5 be properly fixed to the head 3 of the testee 2.

Further, in the abovementioned embodiment, explanation is given for a case where the present invention is applied to the head mount type vision testing device. However, the present invention is not limited thereto, and the vision testing device other than the head mount type can also be used.

Further, in the abovementioned embodiment, the planar display device 12 is configured by using the liquid crystal display device. However, the present invention is not limited thereto, and an organic EL (Electro Luminescence) display device can also be used.

Further, in the abovementioned embodiment, the display optical system 11 is composed of four lenses in total and the observation optical system 15 is composed of two lenses in total (one of which is shared with the display optical system 11). The number and the shape of the lenses constituting each optical system, and the lens interval in the optical axis direction, etc., can be changed as necessary. However, in order to correct a chromatic aberration and an image magnification by combining the lens having the positive power and the lens having the negative power, it is preferable to constitute the second lens group 21 by a plurality of lenses. Further, the mirror 20 may be configured as a dichroic mirror.

Figure 5:
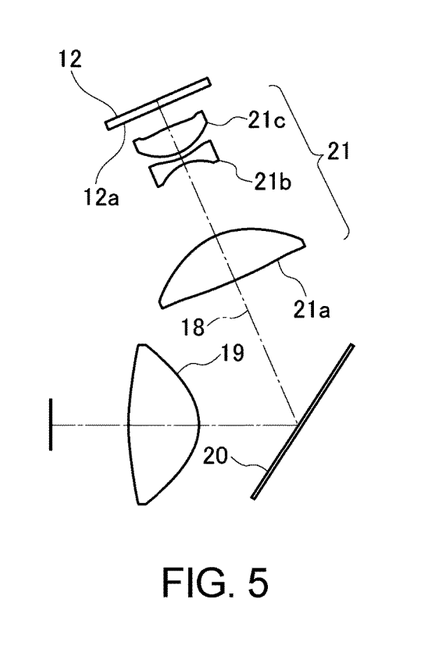
FIG. 5 is a schematic view (No. 1) showing another configuration example of a display optical system.
Figure 6:
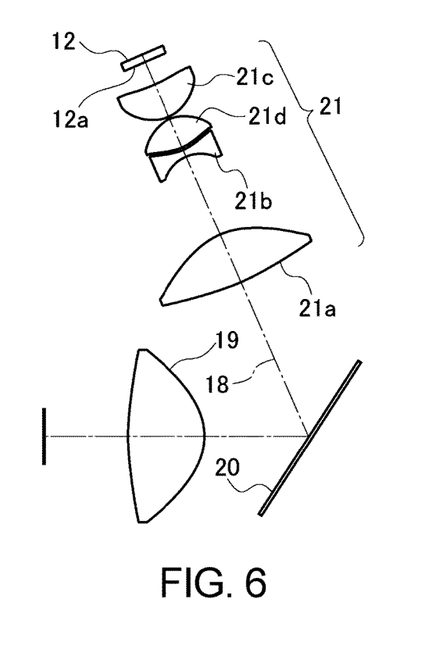
FIG. 6 is a schematic view (part 2) showing another configuration example of a display optical system.

As an example, another configuration example of the display optical system is shown in FIG. 5 and FIG. 6.

In FIG. 5, the lens 21c belonging to the second lens group 21 of the display optical system 11 is made movable in the optical axis direction by a lens moving mechanism (not shown). This point is different from the above embodiment.

When this configuration is adopted, the diopter can be adjusted according to the visual acuity of the testee.

On the other hand, in FIG. 6, the point that the second lens group 21 of the display optical system 11 is configured by using four lenses 21a to 21d in total by adding the lens (convex lens) 21d, and the point that the size of the display surface 12a of the planar display device 12 is reduced, are different from those in the above embodiment. When this configuration is adopted, it becomes possible to display the visual target more clearly for the testee. Also in this configuration, by making the lens 21c moveable in the direction of the optical axis, it becomes possible to adjust the diopter according to the visual acuity of the testee.

DESCRIPTION OF SIGNS AND NUMERALS

1 Vision testing device
2 Testee
3 Head
5 Device main body
6 Mounting fixture
7 Casing
8 Eyeball
9 Pupil
11 Display optical system
12 Planar display device
12a Display surface
15 Observation optical system
16 Imaging device
17 Infrared light source
18 Optical axis (18a, 18b, 18c)
19 First lens
20 Mirror
21 Second lens group
22 Third lens group

The invention claimed is:
1. A vision testing device, comprising:
a planar display device that displays a visual target for a testee who receives a vision test; and
a display optical system provided on an optical axis between an eyeball position where an eyeball of the testee is placed and a display surface of the planar display device, the display optical system being configured by a f-θ optical system including at least an aspherical lens having a proportional relationship between an incident angle θ of a principal ray when the testee views the visual target from the eyeball position through the display optical system and an image height Y on the display surface of the planar display device.
2. The vision testing device according to claim 1, wherein a maximum viewing angle of the display optical system is set in a range of 30 degrees or more and 60 degrees or less at a half angle of view.
3. A head mount type display device used by being mounted on a user's head, the head mount type display device comprising:
a planar display device that displays an image for a user; and
a display optical system provided on an optical axis between an eyeball position where an eyeball of the user is placed and a display surface of the planar display device, the display optical system being configured by a f-θ optical system including at least an aspherical lens having a proportional relationship between an incident angle θ of a principal ray when the user views an image from the eyeball position through the display optical system and an image height Y on the display surface of the planar display device.
4. The head mount type display device according to claim 3, wherein a maximum viewing angle of the display optical system is set in a range of 30 degrees or more and 60 degrees or less at a half angle of view.

* * * * *